(12) United States Patent
Goldmann et al.

(10) Patent No.: US 6,191,157 B1
(45) Date of Patent: Feb. 20, 2001

(54) HETERO-LINKED PHENYLGLYCINOLAMIDES

(75) Inventors: Siegfried Goldmann; Ulrich Müller, both of Wuppertal (DE); Richard Connell, Trumbull, CT (US); Hilmar Bischoff; Dirk Denzer, both of Wuppertal (DE); Rudi Grützmann, Solingen (DE); Martin Beuck, Erkrath (DE)

(73) Assignee: Bayer Aktiengesellschaft, Leverkusen (DE)

( * ) Notice: Under 35 U.S.C. 154(b), the term of this patent shall be extended for 0 days.

(21) Appl. No.: 09/205,772

(22) Filed: Dec. 4, 1998

Related U.S. Application Data

(62) Division of application No. 08/833,826, filed on Apr. 10, 1997.

(30) Foreign Application Priority Data

Apr. 18, 1996 (DE) .............................................. 196 15 262

(51) Int. Cl.[7] ...................... C07D 235/24; C07D 235/28; C07D 233/61; C07D 233/60; A61K 31/415
(52) U.S. Cl. .................. 514/385; 548/304.4; 548/306.4; 548/333.5; 548/333.6; 548/333.61; 548/324.1; 548/328.5; 548/335.5; 548/340.1; 548/335.1; 548/334.1; 548/307.1; 548/307.4; 548/309.7; 548/301.7; 514/400; 514/399; 514/487; 514/396; 514/398; 514/385; 514/394
(58) Field of Search ................................ 548/328.5, 333.5, 548/304.4, 334.1, 306.4, 335.5, 340.1, 335.1, 307.4, 307.1, 324.1, 301.7, 309.7; 514/396, 400, 398, 394, 399

(56) References Cited

U.S. PATENT DOCUMENTS

| 4,970,215 | 11/1990 | Mohrs et al. . |
| 5,578,616 | * 11/1996 | Aslanian et al. ..................... 514/341 |

FOREIGN PATENT DOCUMENTS

| 344519 | 12/1989 | (EP) . |
| 0716082 | * 6/1996 | (EP) . |

OTHER PUBLICATIONS

Heinmann et al. (Aterosclerosis, 61, (1986), pp 219–233.*
Meuller, et al. (CA 125:142580, EP 716082).

* cited by examiner

*Primary Examiner*—Sabiha N. Qazi
(74) *Attorney, Agent, or Firm*—Norris, McLaughlin & Marcus, P.A.

(57) ABSTRACT

The hetero-linked phenylglycinolamides are prepared by reaction of the corresponding hetero-linked phenylacetic acids with appropriate phenylglycinols. The hetero-linked phenylglycinolamides are suitable as active compounds in medicaments.

6 Claims, No Drawings

HETERO-LINKED PHENYLGLYCINOLAMIDES

This Appln is a div of U.S. Ser. No. 08/833,826 filed Apr. 10, 1997.

The present invention relates to hetero-linked phenylglycinolamides, processes for their preparation and their use as medicaments, in particular as antiatherosclerotic medicaments.

It is known that raised blood levels of triglycerides (hypertriglyceridaemia) and cholesterol (hypercholesterolaemia) are associated with the genesis of atherosclerotic vascular wall changes and coronary heart diseases.

A distinctly increased risk of the development of coronary heart diseases moreover exists if these two risk factors occur in combination, which in turn is accompanied by an overproduction of apoliprotein B-100. There is therefore still a great need to make available active medicaments for the control of atherosclerosis and coronary heart diseases.

The present invention relates to hetero-linked phenylglycinolamides of the general formula (I)

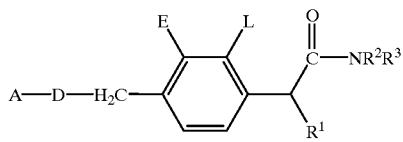

(I)

in which
  A represents aryl having 6 to 10 carbon atoms, benzyl or an optionally benzo-fused 5- to 7-membered saturated, partially unsaturated or unsaturated heterocycle having up to 3 heteroatoms from the series S, N and/or O, the ring systems optionally being substituted—also via the N function—up to 3 times identically or differently by halogen, trifluoromethyl, carboxyl, hydroxyl, nitro, cycloalkyl having 3 to 7 carbon atoms, benzyl, phenyl, benzyloxy or by straight-chain or branched alkyl, alkoxy or alkoxycarbonyl each having up to 6 carbon atoms, or a radical of the formula $R^5R^4N-$ or

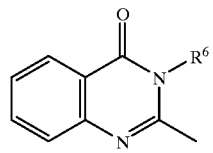

in which
    $R^4$ and $R^5$ are identical or different and denote hydrogen, phenyl or straight-chain or branched alkyl having up to 6 carbon atoms,
    $R^6$ denotes hydrogen, phenyl or straight-chain or branched alkyl having up to 4 carbon atoms,
  D represents an oxygen atom or a radical of the formula $—CO—$, $—(CO)_a—NR^7—$, $—(CH_2)_b S—$, $—(CH_2)_c—NR^8$ or $—CH=CH—$, in which
    a, b and c are identical or different and denote a number 0 or 1,
    $R^7$ and $R^8$ are identical or different and denote hydrogen, straight-chain or branched alkyl or acyl each having up to 6 carbon atoms, phenyl or benzyl, the ring systems optionally being substituted up to 2 times identically or differently by nitro, halogen, trifluoromethyl or by straight-chain or branched alkyl or alkoxy each having up to 3 carbon atoms,
  E and L are identical or different and represent hydrogen, cycloalkyl having 3 to 8 carbon atoms, azido, hydroxyl, halogen, straight-chain or branched alkyl, alkoxy or alkenyl each having up to 6 carbon atoms,
  $R^1$ represents cycloalkyl having 3 to 8 carbon atoms, or represents straight-chain or branched alkyl having up to 10 carbon atoms,
  $R^2$ represents hydrogen or straight-chain or branched alkyl having up to 4 carbon atoms,
  $R^3$ represents a radical of the formula

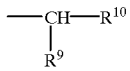

in which
    $R^9$ denotes hydrogen or a radical of the formula $CH_2—OH$,
    $R^{10}$ denotes phenyl which is optionally substituted up to 3 times identically or differently by hydroxyl, halogen or straight-chain or branched alkyl having up to 5 carbon atoms,
  and their salts.

The hetero-linked phenylglycinolamides according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Particularly preferred salts are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

The compounds according to the invention can exist in stereoisomeric forms which either behave as image and mirror image (enantiomers), or which do not behave as image and mirror image (diastereomers). The invention relates both to the enantiomers and to the diastereomers or their respective mixtures. These mixtures of the enantiomers and diastereomers can be separated in a manner known per se into the stereoisomerically uniform constituents.

In the context of the invention heterocycle, optionally benzo-fused, in general represents a saturated, partially unsaturated or unsaturated 5- to 7-membered, preferably 5- to 6-membered, heterocycle which can contain up to 3 heteroatoms from the series S, N and/or O and which in the case of a nitrogen atom can also be bonded via this.

Examples which may be mentioned are: indolyl, quinolyl, benzo[b]thienyl, benzo[b]furyl, pyridyl, thienyl, furyl, pyrrolyl, thiazolyl, oxazolyl, imidazolyl, morpholinyl or piperidyl. Quinolyl, furyl, pyridyl and thienyl are preferred.

Preferred compounds of the general formula (I) according to the invention are those
in which
A represents naphthyl, phenyl, benzyl, pyridyl, imidazolyl, benzimidazolyl or quinolyl, each of which is optionally substituted—also via the N function—up to 3 times identically or differently by fluorine, chlorine, bromine, trifluoromethyl, carboxyl, hydroxyl, nitro, cyclopropyl, cyclopentyl, cyclohexyl, benzyl, phenyl, benzyloxy or by straight-chain or branched alkyl, alkoxy or alkoxycarbonyl each having up to 4 carbon atoms, or a radical of the formula $R^5R^4N$- or

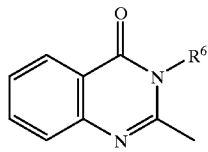

in which
$R^4$ and $R^5$ are identical or different and denote hydrogen, phenyl or straight-chain or branched alkyl having up to 4 carbon atoms,
$R^6$ denotes hydrogen, phenyl or straight-chain or branched alkyl having up to 3 carbon atoms,
D represents an oxygen atom or a radical of the formula —CO—, —(CO)$_a$—NR$^7$, —(CH$_2$)$_b$S—, —(CH$_2$)$_c$—NR$^8$ or —CH═CH—, in which
a, b and c are identical or different and denote a number 0 or 1,
$R^7$ and $R^8$ are identical or different and denote hydrogen, straight-chain or branched alkyl or acyl each having up to 5 carbon atoms, phenyl or benzyl, the ring systems optionally being substituted up to 2 times identically or differently by nitro, fluorine, chlorine, bromine, trifluoromethyl or by straight-chain or branched alkyl or alkoxy each having up to 3 carbon atoms,
E and L are identical or different and represent hydrogen, cyclopropyl, cyclopentyl, cyclohexyl, azido, hydroxyl, fluorine, chlorine, bromine, straight-chain or branched alkyl, alkoxy or alkenyl each having up to 3 carbon atoms,
$R^1$ represents cyclopropyl, cyclobutyl, cyclopentyl, cyclohexyl or cycloheptyl, or straight-chain or branched alkyl having up to 8 carbon atoms,
$R^2$ represents hydrogen or straight-chain or branched alkyl having up to 3 carbon atoms,
$R^3$ represents a radical of the formula,

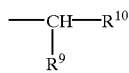

in which
$R^9$ denotes hydrogen or a radical of the formula $CH_2$—OH,
$R^{10}$ denotes phenyl which is optionally substituted up to 2 times identically or differently by hydroxyl, fluorine, chlorine, bromine or straight-chain or branched alkyl having up to 3 carbon atoms,
and their salts.

Particularly preferred compounds of the general formula (I) according to the invention are those
in which
A represents naphthyl, phenyl, benzyl, pyridyl, imidazolyl, benzimidazolyl or quinolyl, each of which is optionally substituted—also via the N function—up to 2 times identically or differently by fluorine, chlorine, trifluoromethyl, carboxyl, hydroxyl, nitro, cyclohexyl, benzyl, phenyl, benzyloxy or by straight-chain or branched alkyl, alkoxy or alkoxycarbonyl each having up to 3 carbon atoms, or a radical of the formula $R^5R^4N$- or

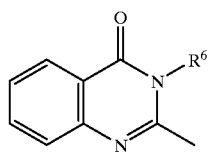

in which
$R^4$ and $R^5$ are identical or different and denote hydrogen, phenyl or methyl,
$R^6$ denotes hydrogen, phenyl or methyl,
D represents an oxygen atom or a radical of the formula —CO—, —(CO)$_a$—NR$^7$, —(CH$_2$)$_b$S—, —(CH$_2$)$_b$)S—, —(CH$_2$)$_c$—NR$^8$ or —CH═CH—, in which
a, b and c are identical or different and denote a number 0 or 1,
$R^7$ and $R^8$ are identical or different and denote hydrogen, methyl, ethyl, acetyl, phenyl or benzyl, the ring systems optionally being substituted up to 2 times identically or differently by nitro, fluorine, chlorine, bromine, trifluoromethyl or by straight-chain or branched alkyl or alkoxy each having up to 3 carbon atoms.
E and L are identical or different and represent hydrogen, fluorine, chlorine or bromine,
$R^1$ represents cyclopropyl, cyclobutyl, cyclopentyl or cyclohexyl or straight-chain or branched alkyl having up to 8 carbon atoms,
$R^2$ represents hydrogen or straight-chain or branched alkyl having up to 3 carbon atoms,
$R^3$ represents a radical of the formula,

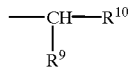

in which
$R^9$ denotes hydrogen or a radical of the formula $CH_2$—OH,
$R^{10}$ denotes phenyl which is optionally substituted up to 2 times identically or differently by hydroxyl, fluorine, chlorine, methyl or ethyl,
and their salts.

Additionally, a process for the preparation of the compounds of the general formula (I) according to the invention has been found, characterized in that carboxylic acids of the general formula (II)

(II)

A—D—CH$_2$—[phenyl with E, L substituents]—CH(R$^1$)—CO$_2$H in which
 A, D, E, L and R$^1$ have the meaning given above, are reacted, optionally with prior activation of the carboxylic acid function, with phenylglycinols of the general formula (III)

HR$^2$—N—R$^3$   (III)

in which
 R$^2$ and R$^3$ have the meaning indicated above, if appropriate under a protective gas atmosphere, if appropriate in inert solvents, in the presence of a base and/or auxiliary.

The process according to the invention can be illustrated by way of example by the following equation:

[Scheme: 1-methyl-2-(4-(carboxy(cyclopentyl)methyl)benzylthio)imidazole + (R)-2-amino-2-phenylethanol → corresponding amide]

Suitable solvents here are inert organic solvents which do not change under the reaction conditions. These include ethers, such as diethyl ether or tetrahydrofuran, halogenohydrocarbons such as dichloromethane, trichloromethane, tetrachloromethane, 1,2-dichloroethane, trichloroethane, tetrachloroethane, 1,2-dichloroethylene or trichloroethylene, hydrocarbons such as benzene, xylene, toluene, hexane, cyclohexane or petroleum fractions, nitromethane, dimethylformamide, acetone, acetonitrile or hexamethylphosphoramide. It is also possible to employ mixtures of the solvents. Dichloromethane, tetrahydrofuran, acetone and dimethylformamide are particularly preferred.

Suitable bases are the customary inorganic or organic bases. These preferably include alkali metal hydroxides such as, for example, sodium or potassium hydroxide, or alkali metal carbonate such as sodium or potassium carbonate, or alkali metal alkoxides such as, for example, sodium or potassium ethoxide, or sodium or potassium methoxide, or organic amines such as triethylamine, picoline or N-methylpiperidine, or amides such as sodium amide or lithium diisopropylamide, or organometallic compounds such as butyllithium or phenyllithium. Sodium and potassium carbonate and triethylamine are preferred.

The base is employed in an amount from 0.6 mol to 5 mol, preferably from 0.7 mol to 2 mol, relative to 1 mol of the compound of the general formula (II).

The reaction is in general carried out in a temperature range from 0° C. to 150° C., preferably from +20° C. to +110° C.

The reaction can be carried out at normal, elevated or at reduced pressure (e.g. 0.5 to 5 bar). In general, it is carried out at normal pressure.

For activation of the carboxylic acid function, in general bases and/or dehydrating reagents such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulfonate or propanephosphonic anhydride or isobutyl chloroformate or benzotriazolyloxy-tris-(dimethylamino)phosphonium hexafluorophosphate or diphenyl phosphoramidate or methanesulphonyl chloride are suitable, if appropriate in the presence of bases such as triethylamine or N-ethylmorpholine or N-methylpiperidine, or dicyclohexylcarbodiimide and N-hydroxysuccinimide.

The acid-binding agents and dehydrating agents are in general employed in an amount from 0.5 to 3 mol, preferably from 1 to 1.5 mol, relative to 1 mol of the corresponding carboxylic acids.

The compounds of the general formula (II) are known in some cases or are new and can be prepared, for example, by reacting compounds of the general formula (IV)

T—H$_2$C—[phenyl with E, L]—CH(R$^1$)—CO$_2$Y   (IV)

in which
 E, L and R$^1$ have the meaning indicated above,
 T represents a typical leaving group such as, for example, chlorine, bromine, iodine, tosylate or mesylate, preferably bromine,
and
 Y represents hydrogen, (C$_1$–C$_4$)-allyl or another base-stable protective group,
with compounds of the general formula (V)

A—H   (V)

in which
 A has the meaning indicated above in inert solvents, if appropriate in the presence of a base, and then removing the esters or the protective group Y according to customary methods.

The compounds of the general formulae (IV) and (V) are known per se or can be prepared by customary methods.

The compounds of the general formula (III) are likewise known or can be prepared by customary methods.

The compounds of the general formula (I) according to the invention have an unforeseeable spectrum of pharmacological action.

They can be used as active compounds in medicaments for the reduction of changes to vascular walls and for the treatment of coronary heart diseases, cardiac insufficiency, brain function disorders, ischaemic cerebral disorders, apoplexy, circulatory disorders, disorders of the microcirculation and thrombosis.

The proliferation of smooth muscle cells furthermore plays a decisive part in the occlusion of vessels. The compounds according to the invention are suitable for inhibiting this proliferation and thus preventing atherosclerotic processes.

The compounds according to the invention are distinguished by a lowering of the ApoB-100-associated lipoproteins (VLDL and its degradation product, such as, for example, LDL), of ApoB-100, of triglycerides and of cholesterol. They thus have useful pharmacological properties which are superior compared with the prior art.

Surprisingly, the action of the compounds according to the invention consists first in a decrease in or complete inhibition of the formation and/or the release of ApoB-100-associated lipoproteins from liver cells, which results in a lowering of the VLDL plasma level. This lowering of VLDL has to be accompanied by a lowering of the plasma levels of ApoB-100, LDL, triglycerides and of cholesterol; thus simultaneously several of the abovementioned risk factors which are involved in vascular wall changes are lowered.

The compounds according to the invention can therefore be employed for the prevention and treatment of atherosclerosis, obesity, pancreatitis and constipation.

1. Inhibition Of The Release Of ApoB-100-Associated Lipoproteins

The test for detecting the inhibition of the release of ApoB-100-associated lipoproteins from liver cells was carried out in vitro using cultured liver cells, preferably using cells of the human line HepG2. These cells were cultured under standard conditions in medium for the culture of eukaryotic cells, preferably in RPMI 1640 using 10% foetal calf serum. HepG2 cells synthesize and secrete into the culture supernatant ApoB-100-associated lipoprotein particles which in principle are built up in a similar manner to the VLDL and LDL particles which are to be found in the plasma.

These particles can be detected using an immunoassay for human LDL. This immunoassay is carried out using antibodies which have been induced under standard conditions against human LDL in rabbits. The anti-LDL antibodies (rabbit anti-LDL ABs) were purified by affinity chromatography on an immunosorbent using human LDL. These purified rabbit anti-LDL ABs are adsorbed on the surface of plastic. Expediently, this adsorption is carried out on the plastic surface of microtitre plates having 96 wells, preferably on MaxiSorp plates. If ApoB-100-associated particles are present in the supernatant of Hep-G2 cells, then these can bind to the insolubilized rabbit anti-LDL ABs, and an immune complex results which is bound to the plastic surface. Non-bound proteins are removed by washing. The immune complex situated on the plastic surface is detected using monoclonal antibodies which have been induced against human LDL and purified under standard conditions. These antibodies were conjugated with the enzyme peroxidase. Peroxidase converts the colourless substrate TMB into a coloured product in the presence of $H_2O_2$. After acidification of the reaction mixture with $H_2SO_4$, the specific light adsorption at 450 nm is determined, which is a measure of the amount of ApoB-100-associated particles which has been secreted into the culture supernatant by the HepG2 cells.

Surprisingly, the compounds according to the invention inhibit the release of ApoB-100-associated particles. The $IC_{50}$ indicates at which substance concentration the light adsorption is inhibited by 50% in comparison to the control (solvent control without substance).

2. Determination Of VLDL Secretion In Vivo In The Hamster

The effect of the test substances on VLDL secretion in vivo is investigated in the hamster. To do this, golden hamsters are anaesthetized with Ketavet (83 mg/kg s.c.) and Nembutal (50 mg/kg. i.p.) after premedication with atropine (83 mg(kg s.c.). When the animals have become reflex-free, the jugular vein is exposed and cannulated. 0.25 ml/kg of a 20% strength solution of Triton WR-1339 in physiological saline solution is then administered. This detergent inhibits the lipoprotein lipase and thus leads to a rise in the triglyceride level on account of an absent catabolism of secreted VLDL particles. This triglyceride rise can be used as a measure of the VLDL secretion rate. Blood is taken from the animals by puncture of the retroorbital venous plexus before and one and two hours after administration of the detergent. The blood is incubated for two hours at room temperature, then overnight at 4° C. in order to end clotting completely. It is then centrifuged at 10,000 g for 5 minutes. In the serum thus obtained, the triglyceride concentration is determined with the aid of a modified commercially available enzyme test (Merckotest® triglyceride No. 14354). 100 µl of serum are treated with 100 µl of test reagent in 96-hole plates and incubated at room temperature for 10 minutes. The optical density is then determined at a wavelength of 492 nm in an automatic plate-reading apparatus (SLT spectra). Serum samples having too high a triglyceride concentration are diluted with physiological saline solution. The triglyceride concentration contained in the samples is determined with the aid of a standard curve measured in parallel. In this model, test substances are administered intravenously either immediately before administration of the detergent or orally or subcutaneously before initiation of anaesthesia.

3. Inhibition Of Intestinal Triglyceride Absorption In Vivo (Rats)

The substances which are to be investigated for their triglyceride absorption-inhibiting action in vivo are administered to male Wistar rats having a body weight of between 170 and 230 g. For this purpose, the animals are divided into groups of 6 animals 18 hours before administration of substance and the feed is then withdrawn from them. Drinking water is available to the animals ad libitum. The animals of the control groups receive an aqueous tragacanth suspension or a tragacanth suspension which contains olive oil. The tragacanth-olive oil suspension is prepared using the Ultra-Turrax. The substances to be investigated are suspended in a corresponding tragacanth-olive oil suspension, likewise using the Ultra-Turrax, directly before substance administration.

Blood is taken from each rat by puncture of the retroorbital venous plexus before stomach tube application to determine the basal serum triglyceride content. The tragacanth suspension, the tragacanth-olive oil suspensions without substance (control animals), or the substances suspended in a corresponding tragacanth-olive oil suspension are then administered to the fasting animals using a stomach tube. Further taking of blood to determine the postprandial serum triglyceride rise is generally carried out 1, 2 and 3 hours after stomach tube application.

The blood samples are centrifuged and, after recovering the serum, the triglycerides are determined photometrically using an EPOS analyzer 5060 (Eppendorf Gerätebau, Netheler & Hinz GmbH, Hamburg). The determination of the triglycerides is carried out completely enzymatically using a commercially available UV test.

The postprandial serum triglyceride rise is determined by subtraction of the triglyceride preliminary value of each animal from its corresponding postprandial triglyceride concentrations (1, 2 and 3 hours after administration).

The differences (in mmol/l) at each time (1, 2 and 3 hours) are averaged in the groups, and the average values of the serum triglyceride level (ΔTG) of the substance-treated animals are compared with the animals which received only the tragacanth-oil suspension.

The serum triglyceride course of the control animals which received only tragacanth is likewise calculated. The substance effect at each time (1, 2 or 3 hours) is determined as follows and indicated in Δ% of the oil-loaded control.

$$\Delta\% \text{ triglyceride rise} = \frac{\Delta TG_{substance} - \Delta TG_{tragacanth\ control}}{\Delta TG_{oil\ loading} - \Delta TG_{tragacanth\ control}} \times 100$$

Effect of 10 mg of test substance/kg of body weight p.o. on the triglyceride rise (Δ%) 2 h after a triglyceride loading in the serum of fasting rats. The serum triglyceride rise of fat-loaded control animals relative to the serum triglyceride level of tragacanth control animals corresponds to 100%. n=6 animals per group.

Statistical analysis is carried out using Student's t-test after prior checking of the variances for homogeneity.

Substances which at one time statistically significantly (p<0.05) reduce the postprandial serum triglyceride rise by at least 30%, compared with the untreated control group, are regarded as pharmacologically active.

4. Inhibition Of VLDL Secretion In Vivo (Rat)

The action of the test substances on VLDL secretion is likewise investigated in the rat. To do this, 500 mg/kg of body weight (2.5 mg/kg) of Triton WR-1339, dissolved in physiological saline solution, is administered intravenously into the tail vein of rats. Triton WR-1339 inhibits lipoprotein lipase and thus leads by inhibition of VLDL catabolism to a rise in the triglyceride and cholesterol level. These rises can be used as a measure of the VLDL secretion rate.

Blood is taken from the animals by puncture of the retroorbital venous plexus before and one and two hours after administration of the detergent. The blood is incubated at room temperature for 1 h for clotting and the serum is recovered by centrifugation at 10,000 g for 20 s. The triglycerides are then determined photometrically at a wavelength of 540 nm by means of a commercially available coupled enzyme test (Sigma Diagnostics®, No. 339). Measurement is carried out with the aid of a likewise coupled enzyme test (Boehringer Mannheim®, No. 1442350) at a wavelength of 546 nm. Samples having triglyceride or cholesterol concentrations which exceed the measuring range of the methods are diluted with physiological saline solution. The determination of the respective serum concentrations is carried out with the aid of standard series measured in parallel. Test substances are administered orally, intravenously or subcutaneously immediately after Triton injection.

The invention additionally relates to the combination of hetero-linked phenylglycinolamides of the general formula (I) with a glucosidase and/or amylase inhibitor for the treatment of familial hyperlipidaemias, of obesity (adiposity) and of diabetes mellitus. Glucosidase and/or amylase inhibitors in the context of the invention are, for example, acarbose, adiposine, voglibose, miglitol, emiglitate, MDL-25637, camiglibose (MDL-73945), tendamistate, AI-3688, trestatin, pradimicin-Q and salbostatin.

The combination of acarbose, miglitol, emiglitate or voglibose with one of the abovementioned compounds of the general formula (I) according to the invention is preferred.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration of approximately 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, it being possible, for example, if water is used as a diluent optionally to use organic solvents as auxiliary solvents.

Administration is carried out in a customary manner, preferably orally or parenterally, in particular perlingually or intravenously.

In the case of parenteral administration, solutions of the active compound can be employed using suitable liquid excipient materials.

In general, it has proved advantageous in the case of intravenous administration to administer amounts of approximately 0.001 to 1 mg/kg, preferably approximately 0.01 to 0.5 mg/kg, of body weight to achieve effective results, and in the case of oral administration the dose is approximately 0.01 to 20 mg/kg, preferably 0.1 to 10 mg/kg, of body weight.

In spite of this, it may, if appropriate, be necessary to depart from the amounts mentioned, mainly depending on the body weight or on the type of administration route, on individual behaviour towards the medicament, the manner of its formulation and the time or interval at which administration takes place. Thus, in some cases it may be adequate to manage with less than the abovementioned minimum amount, while in other cases the upper limit mentioned has to be exceeded. In the case of the administration of larger amounts, it may be advisable to divide these into several individual doses over the course of the day.

Abbreviations in the Experimental Section

Bn=CH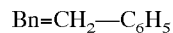

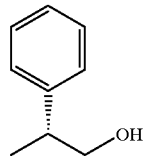

Me=methyl
Et=ethyl
cHex=cyclohexyl
Ph=phenyl

Solvents

C/EA=cyclohexane/ethyl acetate
P/BEA=petroleum ether/ethyl acetate

Starting Compounds

EXAMPLE 1 tert-Butyl N-(2-chlorobenzyl)-2-cyclopentyl-4-(phenylaminomethyl)-phenyl-acetate

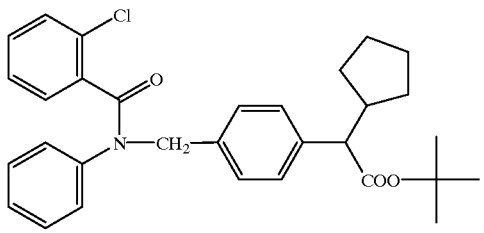

2.3 g (10 mmol) of 2-chlorobenzanilide are dissolved in 10 ml of DMF, and the solution is deprotonated (50° C.) using 330 mg (11 mmol) of NaH (80% strength) and then treated with 3.5 g (10 mmol) of tert-butyl 4-bromomethyl-2-cyclopentyl-acetate (DE 42 00 954 A1) and stirred overnight at RT. It is concentrated, the residue is dissolved in $CH_2Cl_2$, the solution is washed with $H_2O$ and concentrated and the residue is chromatographed on silica gel (cyclohexane/EA= 8:2). 3.8 g (75%) are obtained as a colourless resin.

EXAMPLE II

N-(2-Chlorobenzyl)-2-cyclopentyl-4-(phenylaminomethyl)-phenyl-acetic acid

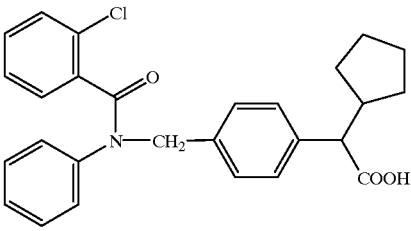

3.5 g (7 mmol) of the compound from Example I are dissolved in 14 ml of dioxane, and the solution is treated with 2 ml of conc. HCl and refluxed for 5 h. It is concentrated, the residue is taken up in $CH_2Cl_2$ and the solution is washed with water. 3 g (96%) of the title compound are obtained as an oil.

The examples listed in Tables I–III are prepared in analogy to the procedure of Example II.

TABLE I

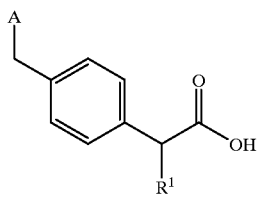

| Ex. no. | A | $R^1$ | m.p. (° C.) | $R_f$ |
|---|---|---|---|---|
| III | ![2-Cl-C6H4-C(=O)-N(Ph)-] | (R&S) cPent | | 0.28 C/EA 1:1 |
| IV | ![2-Cl-C6H4-C(=O)-N(Ph)-] | (R&S) cHept | | 0.3 C/EA 1:1 |
| V | ![C6H5-C(=O)-N(C2H4-O-CH3)-] | (R&S) cPent | | 0.32 C/EA 1:1 |
| VI | ![C6H5-C(=O)-N(C2H4-O-CH3)-] | (R&S) cHept | | 0.46 C/EA 1:1 |

TABLE I-continued

| Ex. no. | A | R¹ | m.p. (° C.) | R_f |
|---|---|---|---|---|
| VII | 2-MeO-C6H4-C(=O)-N(Ph)(Me) | (R&S) cPent | | 0.23 C/EA 1:1 |
| VIII | 2-MeO-C6H4-C(=O)-N(Ph)(Me) | (R&S) cHept | | 0.19 C/EA 1:1 |
| IX | 2-O2N-C6H4-N(Me)(CH2-C6H5) | (R&S) cPent | | 0.22 C/EA 1:1 |
| X | 2-O2N-C6H4-N(Me)(CH2-C6H5) | (R&S) cHept | | 0.28 C/EA 1:1 |
| XI | C6H5-N(Me)(CH2-C6H5) | (R&S) cPent | | 0.25 C/EA 1:1 |
| XII | C6H5-N(Me)(CH2-C6H5) | (R&S) cHept | | 0.33 C/EA 1:1 |
| XIII | 4-MeO-C6H4-N(Me)(CH2-C6H5) | (R&S) cPent | | 0.29 C/EA 1:1 |
| XIV | 4-MeO-C6H4-N(Me)(CH2-C6H5) | (R&S) cHept | | 0.35 C/EA 1:1 |

TABLE I-continued

| Ex. no. | A | R¹ | m.p. (° C.) | $R_f$ |
|---|---|---|---|---|
| XV | MeO-C₆H₄-NH- (4-methoxyphenylamino) | (R&S) cPent | 151 | |
| XVI | MeO-C₆H₄-NH- (4-methoxyphenylamino) | (R&S) cHept | 155 | |
| XVII | 5-Me-pyridin-2-yl-NH- | (R&S) cPent | | 0.05 C/EA 1:1 |
| XVIII | 5-Me-pyridin-2-yl-NH- | (R&S) cHept | | 0.05 C/EA 1:1 |
| XIX | 6-Me-pyridin-2-yl-NH- | (R&S) cPent | | 0.11 (CH₂Cl₂/CH₃OH 95:5) |
| XX | 6-Me-pyridin-2-yl-NH- | (R&S) cHept | 211 | |
| XXI | 4,6-diMe-pyridin-2-yl-NH- | (R&S) cPent | 211 | |
| XXII | 4,6-diMe-pyridin-2-yl-NH- | (R&S) cHept | 190 | |
| XXIII | 4,6-diMe-pyridin-2-yl-N(Ph)- | (R&S) cPent | | 0.58 C/EA 1:1 |

TABLE I-continued

| Ex. no. | A | R¹ | m.p. (° C.) | R_f |
|---|---|---|---|---|
| XXIV | 4,6-dimethyl-2-[N-methyl-N-(2-cyanophenyl)amino]pyridin-2-yl | (R&S) cPent | | 0.11 C/EA 7:3 |
| XXV | 3-methyl-2-(methylamino)pyridin-2-yl | (R&S) cPent | | 0.13 C/EA 1:1 |
| XXVI | 3-methyl-2-(methylamino)pyridin-2-yl | (R&S) cHept | 244 | |
| XXVII | 3-(phenoxymethyl)-2-(methylamino)pyridin-2-yl | (R&S) cPent | 159 | |
| XXVIII | 3-(phenoxymethyl)-2-(methylamino)pyridin-2-yl | (R&S) cHept | | 0.06 C/EA 7:3 |
| XXIX | 2-methyl-N-methylanilino | (R&S) cPent | | |
| XXX | 2-methyl-N-methylanilino | (R&S) cHept | | 0.15 C/EA 7:3 |

TABLE I-continued
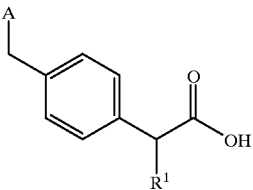
| Ex. no. | A | R¹ | m.p. (° C.) | R_f |
|---|---|---|---|---|
| XXXI | 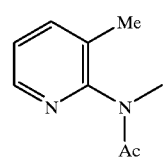 | (R&S) cHept | | |
| XXXII | 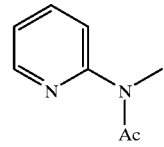 | (R&S) cPent | | |
| XXXIII | 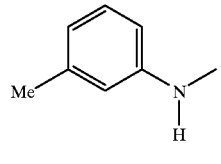 | (R&S) cPent | | 0.42 C/EA 1:1 |
| XXXIV | 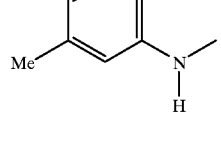 | (R&S) cHept | | 0.15 C/EA 7:3 |
| XXXV | 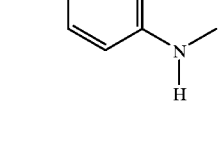 | (R&S) cPent | | 0.13 C/EA 7:3 |
| XXXVI | 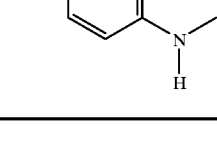 | (R&S) cHept | | 0.18 C/EA 7:3 |

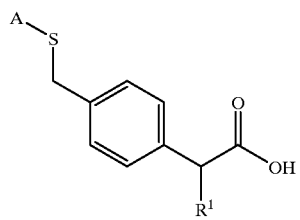
| Ex. no. | A | R¹ | m.p. (° C.) | R_f |
|---|---|---|---|---|
| XXXVII | 1-Me, 2-yl imidazole | (R&S) cPent | 158 | |
| XXXVIII | 1-Me, 2-yl imidazole | (R&S) cHept | | 0.1 C/EA 3:7 |
| XXXIX | 1-Ph, 2-yl imidazole | (R&S) cPent | 184 | |
| XL | 1-Ph, 2-yl imidazole | (R&S) cHept | 139 | |
| XLI | 4,5-diPh, 2-yl imidazole (NH) | (R&S) cPent | | 0.27 C/EA 1:1 |
| XLII | 4,5-diPh, 2-yl imidazole (NH) | (R&S) cHept | 172 | |
| XLIII | 1-Et, 4,5-diPh, 2-yl imidazole | (R&S) cPent | 205 | |

-continued

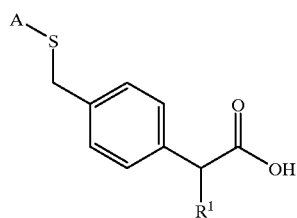

| Ex. no. | A | R¹ | m.p. (° C.) | $R_f$ |
|---|---|---|---|---|
| XLIV | 1-Ethyl-2-methyl-4,5-diphenyl-imidazole | (R&S) cHept | 190 | |
| XLV | 1-cHex-2-methyl-benzimidazole | (R&S) cPent | 197 | |
| XLVI | 1-cHex-2-methyl-benzimidazole | (R&S) cHept | 213 | |
| XLVII | 1-Ph-2-methyl-benzimidazole | (R&S) cPent | 204 | |
| XLVIII | 1-Ph-2-methyl-benzimidazole | (R&S) cHept | 205 | |
| XLIX | 1-CH₂Ph-2-methyl-benzimidazole | (R&S) cPent | 173 | |
| L | 1-CH₂Ph-2-methyl-benzimidazole | (R&S) cHept | 146 | |
| LI | 3-Ph-2-methyl-quinazolin-4(3H)-one | (R&S) cPent | | 0.3 C/EA 7:3 |

-continued

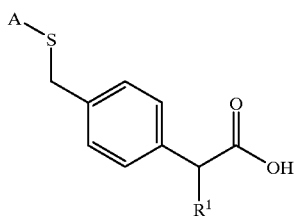

| Ex. no. | A | R¹ | m.p. (° C.) | R$_f$ |
|---|---|---|---|---|
| LII | 2-methylquinolin-3-yl | (R&S) cPent | 119 | |
| LIII | 2-methylquinolin-3-yl | (R&S) cHept | | 0.21 C/EA 7:3 |
| LIV | 2-ethylquinolin-3-yl | (R&S) cPent | 136 | |
| LV | 3-methylnaphthalen-2-yl | (R&S) cPent | 129 | |
| LVI | 2-methylpyridin-3-yl | (R&S) cPent | | 0.42 C/EA 1:1 |
| LVII | 2-methylphenyl | (R&S) cPent | 132 | |
| LVIII | 2-methyl-6-(CO₂Me)phenyl | (R&S) cPent | 183 | |
| LIX | 2-chloro-6-methylphenyl | (R&S) cPent | 134 | |
| LX | 2-chloro-6-methylphenyl | (R&S) cHept | | 0.30 C/EA 7:3 |
| LXI | 2-chloro-6-ethylphenyl | (R&S) cPent | | 0.5 C/EA 1:1 |

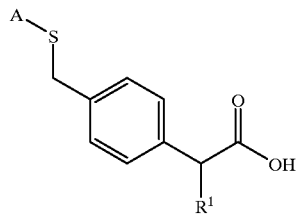

| Ex. no. | A | R¹ | m.p. (° C.) | $R_f$ |
|---|---|---|---|---|
| LXII | 2-CF₃-phenyl-ethyl | (R&S) cPent | | 0.39 C/EA 1:1 |
| LXIII | 2-NO₂-phenyl-ethyl | (R&S) cPent | | 0.29 C/EA 1:1 |

TABLE III

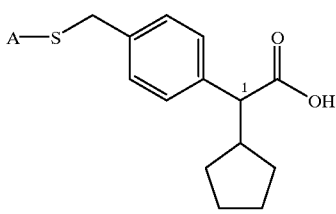

| Ex. no. | A | 1 | m.p. (° C.) | $R_f$ |
|---|---|---|---|---|
| LXIV | 2-naphthylmethyl | R&S | | |
| LXV | quinolin-2-ylmethyl | R&S | | |
| LXVI | pyridin-2-ylmethyl | R&S | | |
| LXVII | benzyl | R&S | | |
| LXVIII | 2-CO₂Me-benzyl | R&S | | |

PREPARATION EXAMPLES

EXAMPLE 1

N-(2-Chlorobenzoyl)-2-cyclopentyl-4-(phenylamino-methyl)-phenyl- [(N'-(2-hydroxy)-1-(R)-phenylethyl)]-2-acetamide

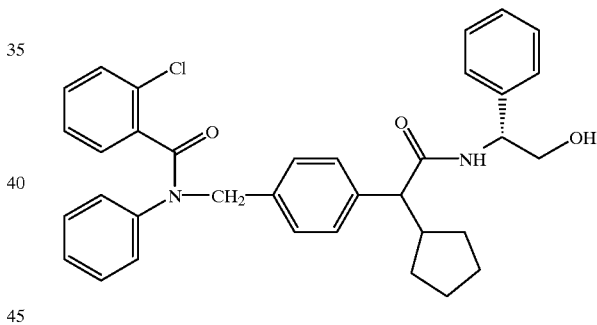

1.34 g (3 mmol) of the compound from Example II are dissolved in 30 ml of CH₂Cl₂ with 0.412 g (3 mmol) of R-(−)-2-phenylglycinol, then 0.446 mg, (3.3 mmol) of 1-hydroxy-1H-benzotriazole hydrate (Aldrich) is added. After addition of 662 mg (3.45 mmol) of N'-(3-dimethylaminopropyl)-N-ethylcarbodiimide hydrochloride (Aldrich) and 0.8 ml of triethylamine, the mixture is stirred at RT overnight. It is diluted with CH₂Cl₂, washed once each with NH₄Cl solution and NaHCO₃ solution, dried and concentrated in a rotary evaporator. It is chromatographed using cyclohexane ethyl acetate (1:1).

Yield: 1.67 g (98%)

$R_f$=0.17 (cyclohexane ethyl acetate=1:1)

The compounds listed in Tables 1–3 are prepared via the corresponding precursors (analogously to Examples I and II) in analogy to the procedure of Example 1:

TABLE 1
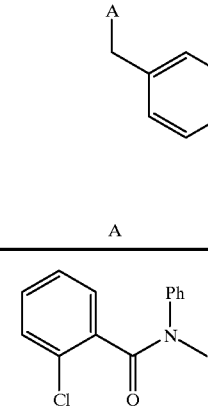
| Ex. no. | A | R¹ | R² | m.p. (° C.) | R_f |
|---|---|---|---|---|---|
| 2 | 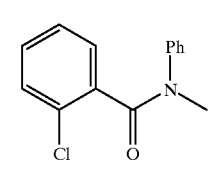 | (R&S) cPent | Bn | 176–177 | |
| 3 | 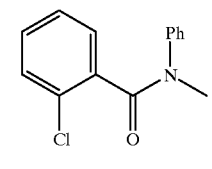 | (R&S) cHept | R-Gly | | 0.23 C/EE 1:1 |
| 4 | 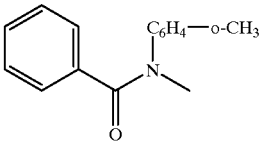 | (R&S) cHept | Bn | 171–172 | |
| 5 | 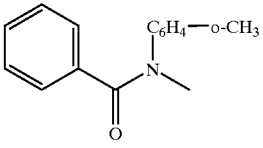 | (R&S) cPent | R-Gly | | 0.21 C/EE 1:1 |
| 6 | 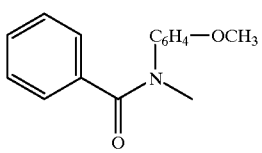 | (R&S) cPent | Bn | 182–183 | |
| 7 | 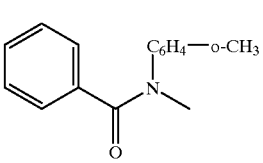 | (R&S) cHept | R-Gly | | 0.26 C/EE 1:1 |
| 8 | 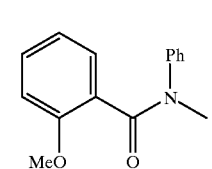 | (R&S) cHept | Bn | 146–147 | |
| 9 |  | (R&S) cPent | R-Gly | | 0.13 C/EE 1:1 |

TABLE 1-continued

| Ex. no. | A | R¹ | R² | m.p. (° C.) | R_f |
|---|---|---|---|---|---|
| 10 | 2-MeO-C₆H₄-C(O)-N(Me)- (Ph on N) | (R&S) cPent | Bn | 171 | |
| 11 | 2-MeO-C₆H₄-C(O)-N(Me)- (Ph on N) | (R&S) cHept | R-Gly | | 0.13 C/EE 1:1 |
| 12 | 2-MeO-C₆H₄-C(O)-N(Me)- (Ph on N) | (R&S) cHept | Bn | 144 | |
| 13 | 2-O₂N-C₆H₄-N(Me)-CH₂-C₆H₅ | (R&S) cPent | R-Gly | | 0.14 C/EE 1:1 |
| 14 | 2-O₂N-C₆H₄-N(Me)-CH₂-C₆H₅ | (R&S) cPent | Bn | | 0.39 C/EE 1:1 |
| 15 | 2-O₂N-C₆H₄-N(Me)-CH₂-C₆H₅ | (R&S) cHept | R-Gly | | 0.17 C/EA 1:1 |
| 16 | 2-O₂N-C₆H₄-N(Me)-CH₂-C₆H₅ | (R&S) cHept | Bn | | 0.44 C/EA 1:1 |
| 17 | 2-H-C₆H₄-N(Me)-CH₂-C₆H₅ | (R&S) cPent | R-Gly | | 0.18 C/EA 1:1 |

TABLE 1-continued

| Ex. no. | A | R¹ | R² | m.p. (° C.) | R_f |
|---|---|---|---|---|---|
| 18 | *N-methyl-N-benzyl aniline* (ortho) | (R&S) cPent | Bn | 160 | |
| 19 | *N-methyl-N-benzyl aniline* (ortho) | (R&S) cHept | R-Gly | | 0.27 C/EA 1:1 |
| 20 | *N-methyl-N-benzyl aniline* (ortho) | (R&S) cHept | Bn | 166 | |
| 21 | *N-methyl-N-benzyl-4-methoxyaniline* | (R&S) cPent | R-Gly | | 0.16 C/EA 1:1 |
| 22 | *N-methyl-N-benzyl-4-methoxyaniline* | (R&S) cPent | Bn | 159 | |
| 23 | *N-methyl-N-benzyl-4-methoxyaniline* | (R&S) cHept | R-Gly | | 0.22 C/EA 1:1 |
| 24 | *N-methyl-N-benzyl-4-methoxyaniline* | (R&S) cHept | Bn | 171 | |
| 25 | *N-methyl-4-methoxyaniline* | (R&S) cPent | R-Gly | | 0.21 C/EA 1:1 |

TABLE 1-continued

| Ex. no. | A | R¹ | R² | m.p. (° C.) | R_f |
|---|---|---|---|---|---|
| 26 | MeO-C₆H₄-NH- (4-MeO-phenyl-NH-) | (R&S) cPent | Bn | 146–147 | |
| 27 | MeO-C₆H₄-NH- | (R&S) cHept | R-Gly | | 0.32 C/EA 1:1 |
| 28 | MeO-C₆H₄-NH- | (R&S) cHept | Bn | 105 | |
| 29 | 5-Me-pyridin-2-yl-NH- | (R&S) cPent | R-Gly | | 0.31 C/EA 1:1 |
| 30 | 5-Me-pyridin-2-yl-NH- | (R&S) cPent | Bn | 133 | |
| 31 | 5-Me-pyridin-2-yl-NH- | (R&S) cHept | R-Gly | | 0.1 C/EA 1:1 |
| 32 | 5-Me-pyridin-2-yl-NH- | (R&S) cHept | Bn | 110–111 | |
| 33 | 6-Me-pyridin-2-yl-NH- | (R&S) cPent | R-Gly | | 0.39 C/EA 4:6 |
| 34 | 6-Me-pyridin-2-yl-NH- | (R&S) cPent | Bn | 159–160 | |
| 35 | 6-Me-pyridin-2-yl-NH- | (R&S) cHept | R-Gly | | 0.17 C/EA 4:6 |
| 36 | 6-Me-pyridin-2-yl-NH- | (R&S) cHept | Bn | 151–152 | |

TABLE 1-continued

| Ex. no. | A | R¹ | R² | m.p. (° C.) | R_f |
|---|---|---|---|---|---|
| 37 | 4,6-dimethyl-2-(NH-)pyridine | (R&S) cPent | R-Gly | | 0.08 C/EA 1:1 |
| 38 | 4,6-dimethyl-2-(NH-)pyridine | (R&S) cPent | Bn | 161–162 | |
| 39 | 4,6-dimethyl-2-(NH-)pyridine | (R&S) cHept | R-Gly | 129–130 | |
| 40 | 4,6-dimethyl-2-(NH-)pyridine | (R&S) cHept | Bn | 155–156 | |
| 41 | 4,6-dimethyl-2-(N(Me)Ph)pyridine | (dia A) cPent | R-Gly | 177 | |
| 42 | 4,6-dimethyl-2-(N(Me)Ph)pyridine | (dia B) cPent | Bn | | 0.40 C/EA 1:1 |
| 43 | 4,6-dimethyl-2-(N(Me)(2-NO₂-C₆H₄))pyridine | (R&S) cPent | R-Gly | | 0.23 C/EA 7:3 |

TABLE 1-continued

| Ex. no. | A | R¹ | R² | m.p. (° C.) | R_f |
|---|---|---|---|---|---|
| 44 | 2,4-dimethyl-6-[N-methyl-N-(2-nitrophenyl)amino]pyridin-... | (R&S) cPent | Bn | | 0.20 C/EA 1:1 |
| 45 | 3-methyl-2-(methylamino)pyridine | (R&S) cPent | R-Gly | | 0.15 C/EA 1:1 |
| 46 | 3-methyl-2-(methylamino)pyridine | (R&S) cPent | Bn | | 0.23 C/EA 7:3 |
| 47 | 3-methyl-2-(methylamino)pyridine | (R&S) cHept | R-Gly | | 0.14 C/EA 1:1 |
| 48 | 3-methyl-2-(methylamino)pyridine | (R&S) cHept | Bn | | 0.23 C/EA 7:3 |
| 49 | 3-(phenoxymethyl)-2-(methylamino)pyridine | (R&S) cPent | R-Gly | 134–135 | |
| 50 | 3-(phenoxymethyl)-2-(methylamino)pyridine | (R&S) cPent | Bn | | 0.23 C/EA 7:3 |

TABLE 1-continued

| Ex. no. | A | R¹ | R² | m.p. (° C.) | R_f |
|---|---|---|---|---|---|
| 51 | pyridine with CH₂OPh and NHMe | (R&S) cHept | R-Gly | | 0.25 C/EA 1:1 |
| 52 | pyridine with CH₂OPh and NHMe | (R&S) cHept | Bn | | 0.31 C/EA 7:3 |
| 53 | phenyl with Me and NHMe | (R&S) cPent | R-Gly | | 0.37 C/EA 1:1 |
| 54 | phenyl with Me and NHMe | (R&S) cPent | Bn | | 0.45 C/EA 7:3 |
| 55 | phenyl with Me and NHMe | (R&S) cHept | R-Gly | | 0.07 C/EA 7:3 |
| 56 | phenyl with Me and NHMe | (R&S) cHept | Bn | 149–150 | |
| 57 | phenyl with Me and N(Me)Ac | (R&S) cHept | Bn | | 0.08 C/EA 4:6 |
| 58 | pyridine with N(Me)Ac | (R&S) cPent | R-Gly | | 0.05 C/EA 4:6 |

TABLE 1-continued
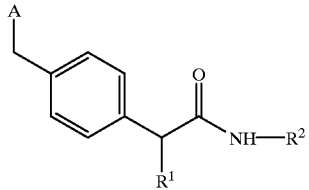
| Ex. no. | A | R¹ | R² | m.p. (° C.) | R$_f$ |
|---|---|---|---|---|---|
| 59 | 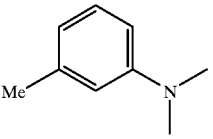 | (R&S) cPent | R-Gly | | 0.34 C/EA 7:3 |
| 60 | 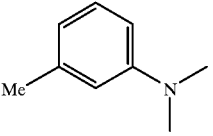 | (R&S) cPent | Bn | | 0.39 C/EA 7:3 |
| 61 | 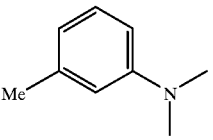 | (R&S) cHept | R-Gly | | 0.13 C/EA 7:3 |
| 62 | 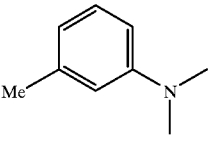 | (R&S) cHept | Bn | | 0.33 C/EA 7:3 |
| 63 | 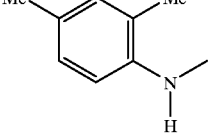 | (R&S) cPent | R-Gly | | 0.37 C/EA 1:1 |
| 64 | 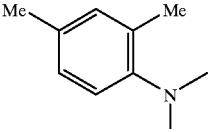 | (R&S) cPent | Bn | | 0.25 C/EA 7:3 |
| 65 | 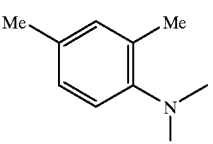 | (R&S) cHept | R-Gly | 0.45 C/EA 1:1 | |
| 66 | 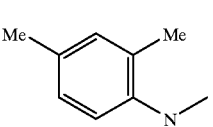 | (R&S) cHept | Bn | | 0.3 C/EA 7:3 |

TABLE 2

[Structure: A-S-CH2-C6H4-CH(R1)-C(=O)-NH-R2]

| Ex. no. | A | R¹ | R² | m.p. (° C.) | R_f |
|---|---|---|---|---|---|
| 67 | 1-Me, 2-yl imidazole | (R&S) cPent | R-Gly | | 0.05 C/EA 3:7 |
| 68 | 1-Me, 2-yl imidazole | (R&S) cPent | Bn | | 0.08 C/EA 1:1 |
| 69 | 1-Me, 2-yl imidazole | (R&S) cHept | R-Gly | 155–156 | |
| 70 | 1-Me, 2-yl imidazole | (R&S) cHept | Bn | | 0.09 C/EA 1:1 |
| 71 | 1-Ph, 2-yl imidazole | (R&S) cPent | R-Gly | | 0.09 C/EA 1:1 |
| 72 | 1-Ph, 2-yl imidazole | (R&S) cPent | Bn | 108–109 | |
| 73 | 1-Ph, 2-yl imidazole | (R&S) cHept | R-Gly | | 0.12 C/EA 1:1 |
| 74 | 1-Ph, 2-yl imidazole | (R&S) cHept | Bn | 144–145 | |

TABLE 2-continued

| Ex. no. | A | R¹ | R² | m.p. (° C.C) | R_f |
|---|---|---|---|---|---|
| 75 | 2-methyl-4,5-diphenyl-1H-imidazole | (R&S) cPent | R-Gly | | 0.22 C/EA 1:1 |
| 76 | 2-methyl-4,5-diphenyl-1H-imidazole | (R&S) cPent | Bn | 140–141 | |
| 77 | 2-methyl-4,5-diphenyl-1H-imidazole | (R&S) cHept | R-Gly | | 0.28 C/EA 1:1 |
| 78 | 2-methyl-4,5-diphenyl-1H-imidazole | (R&S) cHept | Bn | 186–187 | |
| 79 | 1-ethyl-2-methyl-4,5-diphenylimidazole | (R&S) cPent | R-Gly | | 0.25 C/EA 1:1 |
| 80 | 1-ethyl-2-methyl-4,5-diphenylimidazole | (R&S) cPent | Bn | 135–136 | |

TABLE 2-continued

[Structure: A-S-CH2-C6H4-CH(R1)-C(=O)-NH-R2]

| Ex. no. | A | R1 | R2 | m.p. (° C.C) | Rf |
|---|---|---|---|---|---|
| 81 | 1-Et-2-Me-4,5-diPh-imidazole | (R&S) cHept | R-Gly | | 0.33 C/EA 1:1 |
| 82 | 1-Et-2-Me-4,5-diPh-imidazole | (R&S) cHept | Bn | 173–174 | |
| 83 | 1-cHex-2-Me-benzimidazole | (R&S) cPent | R-Gly | | 0.26 C/EA 1:1 |
| 84 | 1-cHex-2-Me-benzimidazole | (R&S) cPent | Bn | | 0.28 C/EA 7:3 |
| 85 | 1-cHex-2-Me-benzimidazole | (R&S) cHept | R-Gly | | 0.37 C/EA 1:1 |
| 86 | 1-cHex-2-Me-benzimidazole | (R&S) cHept | Bn | | 0.39 C/EA 7:3 |
| 87 | 1-Bn-2-Me-benzimidazole | (R&S) cPent | R-Gly | | 0.29 C/EA 1:1 |
| 88 | 1-Bn-2-Me-benzimidazole | (R&S) cPent | Bn | 138–139 | |

TABLE 2-continued

| Ex. no. | A | R¹ | R² | m.p. (° C.C) | R$_f$ |
|---|---|---|---|---|---|
| 89 | 1-benzyl-2-methyl-benzimidazol-yl | (R&S) cHept | R-Gly | | 0.35 C/EA 1:1 |
| 90 | 1-benzyl-2-methyl-benzimidazol-yl | (R&S) cHept | Bn | 164–165 | |
| 91 | 1-benzyl-2-methyl-benzimidazol-yl | (R&S) cPent | R-Gly | 181–182 | |
| 92 | 1-benzyl-2-methyl-benzimidazol-yl | (R&S) cPent | Bn | 154–155 | |
| 93 | 1-benzyl-2-methyl-benzimidazol-yl | (R&S) cHept | R-Gly | | 0.32 C/EA 1:1 |
| 94 | 1-benzyl-2-methyl-benzimidazol-yl | (R&S) cHept | Bn | 158–159 | |
| 95 | 2-methylquinolin-yl | (R&S) cPent | R-Gly | | 0.25 C/EA 1:1 |
| 96 | 2-methylquinolin-yl | (dia A) cPent | R-Gly | 188 | |
| 97 | 2-methylquinolin-yl | (dia B) cPent | R-Gly | 143 | |

TABLE 2-continued
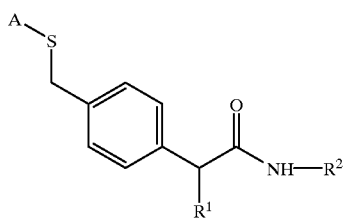
| Ex. no. | A | R¹ | R² | m.p. (° C.C) | R$_f$ |
|---|---|---|---|---|---|
| 98 | 2-methylquinolin-yl | (R&S) cHept | R-Gly | 139–140 | |
| 99 | 2-chlorophenyl | (R&S) cPent | Bn | | 0.43 C/EA 7.3 |
| 100 | 2-chlorophenyl | (R&S) cHept | Bn | | 0.46 C/EA 7:3 |
| 101 | 2-ethylquinolin-yl | (R&S) cPent | R-Gly | | 0.33 C/EA 1:1 |
| 102 | 2-chlorophenyl | (R&S) cPent | R-Gly | 150–151 | |
| 103 | 2-chlorophenyl | (R&S) cPent | R-Gly | 155–156 | |
| 104 | 2-chlorophenyl | (R&S) cPent | R-Gly | 167–168 | |
| 105 | 2-chlorophenyl | (R&S) cPent | R-Gly | 174–175 | |
| 106 | 2-nitrophenyl | (R&S) cPent | R-Gly | 158–160 | |
| 107 | 2-chlorophenyl | (R&S) cHept | R-Gly | 156–157 | |

TABLE 2-continued

[Structure: A-S-CH2-C6H4-CH(R1)-C(=O)-NH-R2]

| Ex. no. | A | R1 | R2 | m.p. (° C.C) | Rf |
|---|---|---|---|---|---|
| 108 | 2-naphthyl | (dia A) cPent | R-Gly | 164 | |
| 109 | quinolin-2-yl | (dia B) cPent | R-Gly | | 0.32 C/EE 1:1 |
| 110 | quinolin-2-yl | (dia A) cPent | R-Gly | 178 | |
| 111 | pyridin-2-yl | (dia B) cPent | R-Gly | | 0.32 C/EE 1:1 |
| 112 | phenyl | (R&S) cPent | R-Gly | 150 | |

TABLE 3

[Structure: A-D-C6H4-CH(R1)-C(=O)-NH-R2]

| Ex. no. | A | D | R1 | R2 | m.p. (° C.) | Rf |
|---|---|---|---|---|---|---|
| 113 | quinolin-2-yl | O | (R&S) cPent | R-Gly | | 0.32 CH2Cl2/CH3OH 100:10 |
| 114 | quinolin-2-yl | CH2—S | (R&S) cPent | R-Gly | 159 | |
| 115 | quinolin-2-yl | CH2—NH | (R&S) cPent | R-Gly | | 0.10 C/EE 1:1 |

TABLE 3-continued
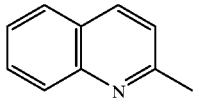
| Ex. no. | A | D | R¹ | R² | m.p. (° C.) | $R_f$ |
|---|---|---|---|---|---|---|
| 116 | 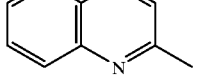 | CH₂—NH | (R&S) cPent | Bn | | 0.35 C/EE 1:1 |
| 117 | 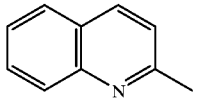 | CO—NH | (R&S) cPent | R-Gly | | 0.22=nl C/EE 1:1 |
| 118 | 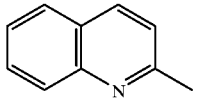 | CO—NH | (R&S) cPent | Bn | 181 | |
| 119 | 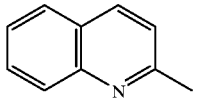 | O—CH₂ | (R&S) cPent | R-Gly | 155 | |
| 120 | 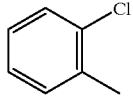 | CH=CH | (R&S) cPent | R-Gly | | 0.6 CH₂Cl₂/EE 1:1 |
| 121 | Me₂NCOS— | — | (R&S) cPent | R-Gly | | 0.10 C/EE 1:1 |
| 122 | 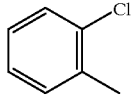 | CH₂—S | (dia A) cPent | R-Gly | 145 | |
| 123 | 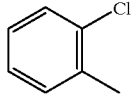 | CH₂—S | (dia B) cPent | R-Gly | 144 | |
| 124 | 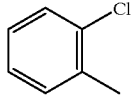 | CH₂—NH | (R&S) cPent | R-Gly | | 0.25 C/EA 1:1 |
| 125 | 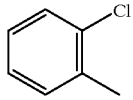 | CH₂—NH | (R&S) cPent | Bn | 112 | |
| 126 |  | CH₂—N(Ac) | (R&S) cPent | R-Gly | 147 | |

TABLE 3-continued

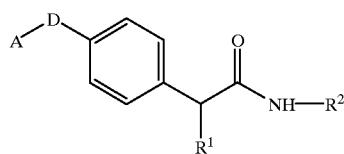

| Ex. no. | A | D | R¹ | R² | m.p. (° C.) | $R_f$ |
|---|---|---|---|---|---|---|
| 127 | 2-Cl-phenyl | CH₂—N(Ac) | (R&S) cPent | Bn | 103 | |
| 128 | 2-Cl-phenyl | CO—NH | (R&S) cPent | | 235 | |
| 129 | 2-NO₂-phenyl | CO—NH | (R&S) cPent | R-Gly | 243 | |

TABLE 4

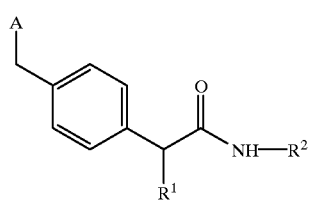

| Ex. no. | A | 1 | m.p. (° C.) | $R_f$ |
|---|---|---|---|---|
| 130 | 2-naphthyl | R&S | | 0.14 C/EA 4:6 |
| 131 | quinolin-2-yl | dia A | 137–139 | |
| 132 | quinolin-2-yl | dia B | | 0.08 C/EA 1:1 |
| 133 | pyridin-2-yl | R&S | | 0.06 C/EA 4:6 |
| 134 | phenyl | R&S | 166–167 | |

TABLE 4-continued

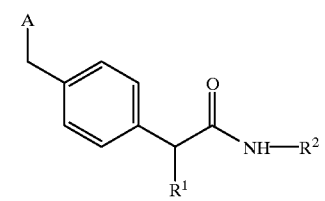

| Ex. no. | A | 1 | m.p. (° C.) | $R_f$ |
|---|---|---|---|---|
| 135 | 2-CO₂Me-phenyl | R&S | | 0.09 C/EA 4:6 |

What is claimed is:

1. A hetero-linked phenylglycinolamide of the formula (I):

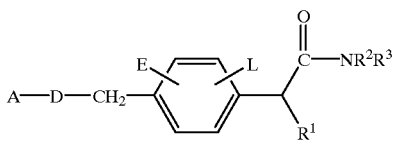

in which

A represents imidazolyl or benzimidazolyl, each of which is optionally substituted, optionally also via a nitrogen atom thereof, by 1 to 3 substituents independently selected from the group consisting of:
a) halogen,
b) trifluoromethyl,
c) carboxyl,
d) hydroxyl, e) nitro,
f) cycloalkyl having 3 to 7 carbon atoms,
g) benzyl,
h) phenyl,
i) benzyloxy,
j) straight-chain or branched alkyl having up to 6 carbon atoms,
k) straight-chained or branched alkoxy having up to 6 carbon atoms; or
l) straight-chain or branched alkoxycarbonyl having up to 6 carbon atoms, D represents an oxygen atom or a radical of the formula

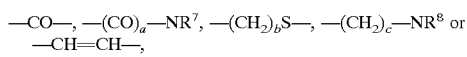
—CO—, —(CO)$_a$—NR$^7$, —(CH$_2$)$_b$S—, —(CH$_2$)$_c$—NR$^8$ or —CH=CH—, in which
a, b and c are identical or different and denote a number 0 or 1,
R$^7$ and R$^8$ are identical or different and denote hydrogen, straight-chain or branched alkyl or acyl each having up to 6 carbon atoms, phenyl or benzyl, the phenyl or benzyl optionally being substituted up to 2 times identically or differently by nitro, halogen, trifluoromethyl or by straight-chain or branched alkyl or alkoxy each having up to 3 carbon atoms,
E and L are identical or different and represents hydrogen, cycloalkyl having 3 to 8 carbon atoms, azido, hydroxyl, halogen, straight-chain or branched alkyl, alkoxy or alkenyl each having up to 6 carbon atoms,
R$^1$ represents cycloalkyl having 3 to 8 carbon atoms, or represents straight-chain or branched alkyl having up to 10 carbon atoms,
R$^2$ represents hydrogen or straight-chain or branched alkyl having up to 4 carbon atoms,
R$^3$ represents a radical of the formula

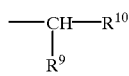

in which
R$^9$ denotes hydrogen or a radical of the formula CH$_2$—OH,
R$^{10}$ denotes phenyl which is optionally substituted up to 3 times identically or differently by hydroxyl, halogen or straight-chain or branched alkyl having up to 5 carbon atoms,
or a salt thereof.

2. A hetero-linked phenylglycinolamide of the formula (I) according to claim 1, in which
A represents imidazolyl or benzimidazolyl, each of which is optionally substituted, optionally also via a nitrogen atom thereof, by 1 to 3 substituents independently selected from the group consisting of:
a) fluorine,
b) chlorine,
c) bromine,
d) trifluoromethyl,
e) carboxyl,
f) hydroxyl,
g) nitro,
h) cyclopropyl,
i) cyclopentyl,
j) cyclohexyl,
k) benzyl,
l) phenyl,
m) benzyloxy,
n) straight-chain or branched alkyl having up to 4 carbon atoms,
o) straight-chain or branched alkoxy having up to 4 carbon atoms; or
p) straight-chain or branched alkoxycarbonyl having up to 4 carbon atoms, D represents an oxygen atom or a radical of the formula

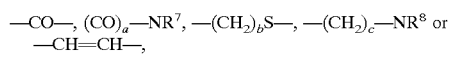
—CO—, (CO)$_a$—NR$^7$, —(CH$_2$)$_b$S—, —(CH$_2$)$_c$—NR$^8$ or —CH=CH—, in which
a, b and c are identical or different and denote a number 0 or 1,
R$^7$ and R$^8$ are identical or different and denotes hydrogen, straight-chain or branched alkyl or acyl each having up to 5 carbon atoms, phenyl or benzyl, the phenyl or benzyl optionally being substituted up to 2 times identically or differently by nitro, fluorine, chlorine, bromine, trifluoromethyl or by straight-chain or branched alkyl or alkoxy each having up to 3 carbon atoms,
E and L are identical or different and represent hydrogen, cyclopropyl, cyclopentyl, cyclohexyl, azido, hydroxyl, fluorine, chlorine, bromine, straight-chain or branched alkyl, alkoxy or alkenyl each having up to 3 carbon atoms,
R$^1$ represents cyclopropyl, cyclobutyl, cyclopentyl cyclohexyl or cycloheptyl, or straight-chain or branched alkyl having up to 8 carbon atoms,
R$^2$ represents hydrogen or straight-chain or branched alkyl having up to 3 carbon atoms,
R$^3$ represents a radical of the formula,

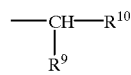

in which
R$^9$ denotes hydrogen or a radical of the formula CH$_2$—OH,
R$^{10}$ denotes phenyl, which is optionally substituted up to 2 times identically or differently by hydroxyl, fluorine, chlorine, bromine or straight-chain or branched alkyl having up to 3 carbon atoms,
or a salt thereof.

3. A hetero-linked phenylglycinolamide of the formula (I) according to claim 1, in which
A represents imidazolyl or benzimidazolyl, each of which is optionally substituted, optionally also via a nitrogen atom thereof, by 1 to 2 substituents independently selected from the group consisting of:
a) fluorine,
b) chlorine,
c) trifluoromethyl,
d) carboxyl,
e) hydroxyl,
f) nitro, g) cyclohexyl,
h) benzyl,
i) phenyl,
j) benzyloxy,
k) straight-chain or branched alkyl having up to 3 carbon atoms,
l) straight-chain or branched alkoxy having up to 3 carbon atoms; or
m) straight-chain or branched alkoxycarbonyl having up to 3 carbon atoms, D represents an oxygen or a radical of the formula

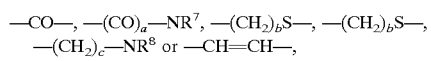

in which
a, b and c are identical or different and denote a number 0 or 1,
$R^7$ and $R^8$ are identical or different and denote hydrogen, methyl, ethyl, acetyl, phenyl or benzyl, the phenyl or benzyl optionally being substituted up to 2 times identically or differently by nitro, fluorine, chlorine, bromine, trifluoromethyl or by straight-chain or branched alkyl or alkoxy each having up to 3 carbon atoms,
E and L are identical or different and represents hydrogen, fluorine, chlorine or bromine,
$R^1$ represents cyclopropyl, cyclobutyl, cyclopentyl or cyclohexyl or straight-chain or branched alkyl having up to 8 carbon atoms,
$R^2$ represents hydrogen or straight-chain or branched alkyl having up to 3 carbon atoms, $R^3$ represents a radical of the formula,

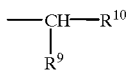

in which
$R^8$ denotes hydrogen or a radical of the formula $CH_2\text{—}OH$,
$R^{10}$ denotes phenyl which is optionally substituted up to 2 times identically or differently by hydroxyl, fluorine, chlorine, methyl or ethyl,
or a salt thereof.

4. Hetero-linked phenylglycinolamide according to claim 1 wherein such compound is N-methyl4-(imidazol-2-yl-thiomethyl)phenyl-2-cyclopentyl-[N'-benzyl]-acetamide of the formula

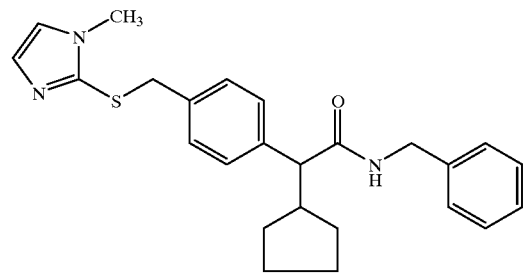

or a salt thereof.

5. A composition for the treatment of atherosclerosis comprising an amount effective therefore of a compound or salt thereof according to claim 1 and a pharmacologically acceptable diluent.

6. The method of treating atherosclerosis in a patient in need thereof which comprises administering to such patient an amount effective therefore of a compound or salt thereof according to claim 1.

* * * * *

UNITED STATES PATENT AND TRADEMARK OFFICE
CERTIFICATE OF CORRECTION

PATENT NO.     : 6,191,157 B1
DATED          : February 20, 2001
INVENTOR(S)    : Siegfried Goldmann et al.

It is certified that error appears in the above-identified patent and that said Letters Patent is hereby corrected as shown below:

Column 64,
Line 8, change "$R^8$" to -- $R^9$ --

Signed and Sealed this

Sixteenth Day of September, 2003

JAMES E. ROGAN
*Director of the United States Patent and Trademark Office*